(12) United States Patent
Nemoto et al.

(10) Patent No.: US 8,805,700 B2
(45) Date of Patent: Aug. 12, 2014

(54) MEDICAL IMAGE SYSTEM

(75) Inventors: Shigeru Nemoto, Tokyo (JP); Nobuhisa Tano, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 132 days.

(21) Appl. No.: 12/293,069

(22) PCT Filed: Mar. 13, 2007

(86) PCT No.: PCT/JP2007/054956
§ 371 (c)(1),
(2), (4) Date: Sep. 15, 2008

(87) PCT Pub. No.: WO2007/105726
PCT Pub. Date: Sep. 20, 2007

(65) Prior Publication Data
US 2009/0043607 A1 Feb. 12, 2009

(30) Foreign Application Priority Data

Mar. 14, 2006 (JP) ................................. 2006-069085

(51) Int. Cl.
*G06Q 50/00* (2012.01)
(52) U.S. Cl.
USPC .................... 705/2; 600/300; 600/432; 705/3
(58) Field of Classification Search
USPC .................. 705/2, 3; 604/121, 232, 131, 241; 606/34; 600/432, 300
See application file for complete search history.

(56) References Cited

U.S. PATENT DOCUMENTS

| 4,624,658 | A | * | 11/1986 | Mardorf et al. | 604/121 |
| 5,814,023 | A | * | 9/1998 | Fulk et al. | 604/232 |
| 6,270,455 | B1 | * | 8/2001 | Brown | 600/300 |
| 6,358,245 | B1 | * | 3/2002 | Edwards et al. | 606/34 |

(Continued)

FOREIGN PATENT DOCUMENTS

| JP | 08-509402 A | 10/1996 |
| JP | 2002-083062 A | 3/2002 |

(Continued)

OTHER PUBLICATIONS

Nakajima, T. 2002 "Hoshasen Bumon Joho Kanri System Tosrim™ V3" *Medical Review* 26(2):64-68.

*Primary Examiner* — Hiep V Nguyen
*Assistant Examiner* — Teresa Woods
(74) *Attorney, Agent, or Firm* — Knobbe, Martens Olson & Bear, LLP

(57) ABSTRACT

A medical image system comprises a medical imaging apparatus, an injector, and a hospital management server having database. The injector has (a) communicating means for allowing communication with the hospital management server; and (b) a patient identifying portion which includes a detecting means for detecting patient-specific information and a means for transmitting the recognized information, further comprising (c) checking means being provided for at least one of the hospital management server and the injector or being provided as a separate apparatus, the means receives information transmitted from the patient identifying portion, and checks the received information to identify the patient.

6 Claims, 4 Drawing Sheets

(56) References Cited

U.S. PATENT DOCUMENTS

| | | | |
|---|---|---|---|
| 7,419,478 B1* | 9/2008 | Reilly et al. | 604/241 |
| 7,553,294 B2* | 6/2009 | Lazzaro et al. | 604/131 |
| 2004/0064041 A1* | 4/2004 | Lazzaro et al. | 600/432 |
| 2004/0116861 A1* | 6/2004 | Trocki et al. | 604/131 |
| 2004/0253083 A1* | 12/2004 | Gambarelli et al. | 414/416.01 |
| 2005/0010447 A1* | 1/2005 | Miyasaka et al. | 705/3 |
| 2005/0234337 A1* | 10/2005 | Browne | 600/432 |
| 2009/0312632 A1* | 12/2009 | Hack | 600/432 |

FOREIGN PATENT DOCUMENTS

| | | |
|---|---|---|
| JP | 2002-119587 | 4/2002 |
| JP | 2003-030324 | 1/2003 |
| JP | 2003-114933 | 4/2003 |
| JP | 2003-225305 | 8/2003 |
| JP | 2004-258833 | 9/2004 |
| JP | 2004-348717 | 9/2004 |
| JP | 2005-198808 | 7/2005 |
| JP | 2005-278727 | 10/2005 |
| WO | WO 94/25089 A1 | 11/1994 |

\* cited by examiner

MEDICAL IMAGE SYSTEM

This application is U.S. National Phase of International Application PCT/JP2007/054956, filed Mar. 13, 2007 designating the U.S., and published in English as WO 2007/105726 on Sep. 20, 2007, which claims priority to Japanese Patent Application No. 2006-069085 filed Mar. 14, 2006.

TECHNICAL FIELD

The present invention relates to a system which comprises a medical imaging diagnostic apparatus and a chemical liquid injector, the system takes a diagnostic image of a patient who is injected with a chemical liquid, and displays it.

BACKGROUND ART

Presently available medical imaging diagnostic apparatuses include X-ray CT (Computed Tomography) scanners, MRI (Magnetic Resonance Imaging) apparatuses, PET (Positron Emission Tomography) apparatuses, ultrasonic diagnostic apparatuses, CT angiography apparatuses, MRA (MR angiography) apparatuses and the like.

An image information taken by such a medical imaging diagnostic apparatus (hereinafter referred to simply as an imaging apparatus) is displayed in an image viewer operated by a doctor, or is recorded on an image server in a filing room with a commercially practical image recording/reproducing system (see, for example, Patent Document 1 (Japanese Patent Laid-Open No. 2003-114933)).

When the imaging apparatus is used, chemical liquid such as contrast medium, radioactive material, or physiological saline is often injected into a patient in order to provide favorable diagnostic images and for other reasons. Chemical liquid injectors for automatically injecting the chemical liquid have been put into practical use. To prevent use of a wrong type of syringe in the injection, some proposals have conventionally been made, for example, to provide a system which includes a syringe having a data carrier means such as an IC chip for storing chemical data and an injector having a data receiving means (see, for example, Patent Document 2 (Japanese Patent No. 3323204)).

On the other hand, a system for identifying a patient inside and outside a hospital has been proposed to prevent patient mix-ups and smoothly conduct medical practice. A known method for patient identification involves recognition of information in a barcode or on an IC chip (RF tag) embedded in a patient wristband, a fingerprint, an iris or the like by using a portable terminal (PDA) (see Patent Document 3 (Japanese Patent Laid-Open No. 2004-348717) and Patent Document 4 (Japanese Patent Laid-Open No. 2005-278727)).

The conventional systems, however, require the portable terminal (PDA) for patient identification. It is thus necessary to reserve a space, albeit small, for placing the terminal, and placing the small device may disturb the site for medical practice. In this manner, the injector and the patient identification system have conventionally been provided as independent systems, without any contemplation of information exchange, communication, or coordination performed between them.

Aside from the patient identification, Patent Document 5 (Japanese Patent Laid-Open No. 2005-198808) has proposed a system in which injection data is sent to a computer and it is displayed on a display together with a diagnostic image. Patent Document 5, however, has not described transmission or reception of data to or from a management server in a hospital. Thus, there has been a need to provide a system in which image data and injection data are managed in a unified manner and applied usefully to the next test or treatment.

Patent Document 1: Japanese Patent Laid-Open No. 2003-114933
Patent Document 2: Japanese Patent No. 3323204
Patent Document 3: Japanese Patent Laid-Open No. 2004-348717
Patent Document 4: Japanese Patent Laid-Open No. 2005-278727
Patent Document 5: Japanese Patent Laid-Open No. 2005-198808

DISCLOSURE OF THE INVENTION

It is an object of the present invention to provide a medical image system in which any extra device does not need to be provided in a site where a medical diagnostic image is taken, patient identification is reliably performed, and test results are transmitted to a management server in a hospital in order to allow unified management of the information.

It is another object of the present invention to provide a system in which image data and injection data are managed in a unified manner, and in which the data may be used to the next test or treatment.

The present invention relates to the following.
1. A medical image system comprising:
    (i) a medical imaging apparatus;
    (ii) an injector which includes a piston driving mechanism and a control mechanism, to inject chemical liquid into a patient, the piston driving mechanism holding a syringe including a cylinder and a syringe piston to move the syringe piston relative to the cylinder, and the control mechanism controlling the piston driving mechanism; and
    (iii) a hospital management server which has a database for patient information,
    wherein the injector includes:
    (a) communicating means for allowing communication with the hospital management server; and
    (b) a patient identifying portion which includes a detecting means for detecting patient-specific information and a means for transmitting the recognized information,
    further comprising (c) checking means being provided for at least one of the hospital management server and the injector or being provided as a separate apparatus, the means receives information transmitted from the patient identifying portion, and checks the received information to identify the patient
2. The medical image system according to claim 1, wherein
    the checking means is provided for the hospital management server,
    the injector transmits the patient-specific information obtained in the patient identifying portion, to the checking means provided for the hospital management server via the communicating means, and
    the checking means checks the information against the database in order to perform patient identification.
3. The medical image system according to claim 1, wherein
    the checking means is provided for the injector,
    the injector receives the patient-specific information from the hospital management server via the communicating means, and
    the checking means checks the patient-specific information received from the patient identifying portion, against the patient-specific information received from the hospital management server in order to perform patient identification.
4. The medical image system according to any one of claims 1 to 3, wherein the syringe includes data carrier means for recording syringe information, and the injector includes syringe-information receiving means for receiving the syringe information recorded on the data carrier means.
5. The medical image system according to any one of claims 1 to 4, wherein the injector includes data outputting means for transmitting chemical liquid injection data to the hospital management server.
6. The medical image system according to claim 5, wherein the injector includes means for receiving at least imaging conditions from the medical imaging apparatus, and the data outputting means transmits the received imaging condition data together with the chemical liquid injection data to the hospital management server.
7. An injector used in the medical image system according to any one of claims 1 to 6.

EFFECT OF THE INVENTION

In the medical image system according to the present invention, it is possible to achieve readily patient identification in a site where imaging is performed, and to transmit conveniently the data of the performed injection from the injector and the data of imaging condition from the imaging apparatus as required, to the hospital system. In addition, any extra device such as a portable terminal device (PDA) does not need to be provided separately in the site where imaging is performed, and thus any space for placing the device is unnecessary, thereby preventing any disturbance in the site for medical practice.

DESCRIPTION OF REFERENCE NUMERALS

100 INJECTOR
101 INJECTION CONTROL UNIT
102 CABLE
103 MAIN OPERATION PANEL
104 DISPLAY
107 HAND UNIT
108 CABLE
110 INJECTION HEAD
111 STAND
112 ARM
113 HEAD BODY
114 CONCAVE PORTION
130 PISTON DRIVING MECHANISM
150 COMMUNICATING PORTION
160 COMPUTING PORTION
200C, 200P SYRINGE
210 CYLINDER
220 PISTON
230 CONNECTION TUBE
300 CT APPARATUS
301 SCANNER BODY
302 CONTROL UNIT
400 PATIENT IDENTIFYING PORTION
410 DETECTING PORTION
420 TRANSMITTING PORTION
510 DATA CARRIER MEANS
520 SYRINGE-INFORMATION RECEIVING MEANS
600 HOSPITAL MANAGEMENT SERVER
610 DATABASE
620 CHECKING MEANS

BEST MODE FOR CARRYING OUT THE INVENTION

<Embodiment 1>

Figure 1:
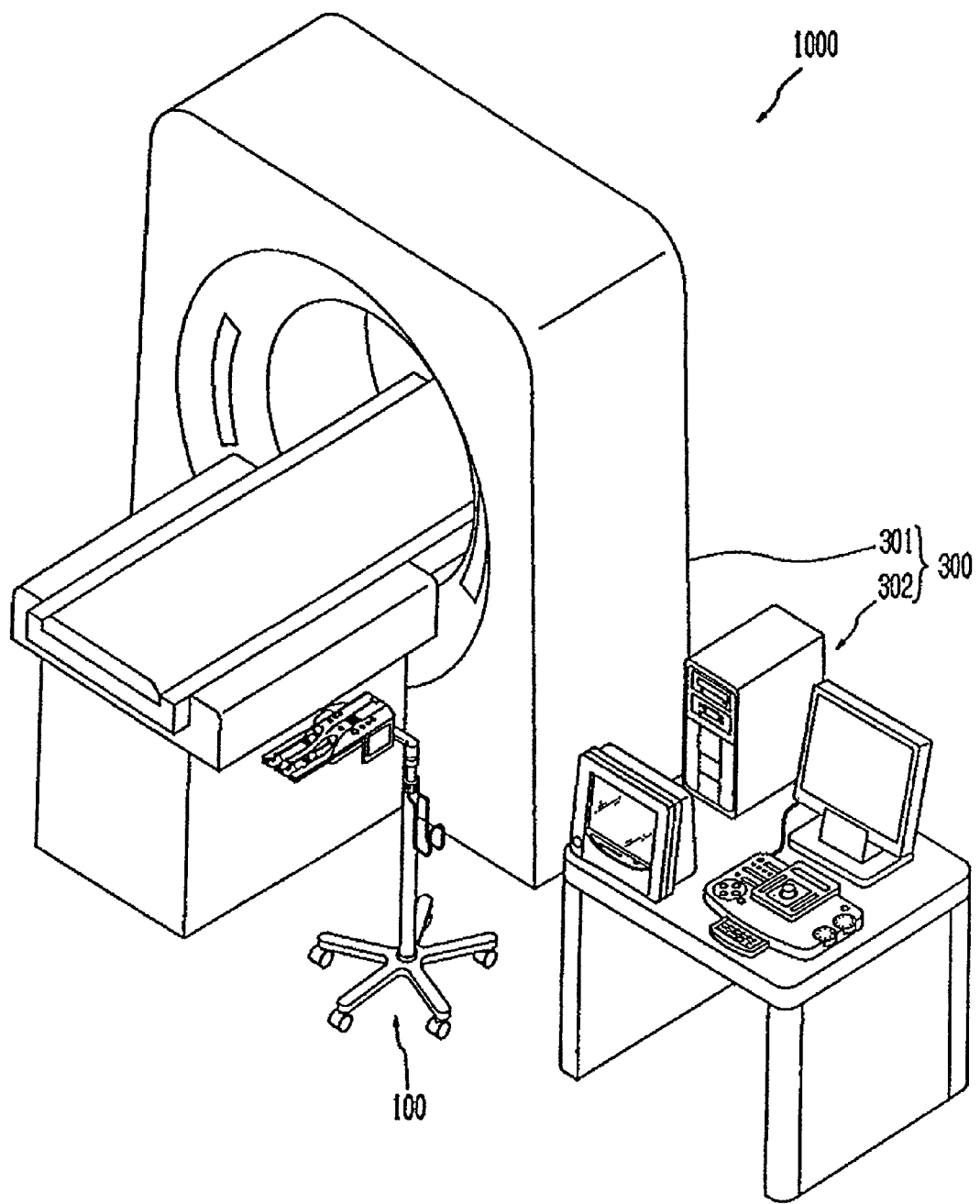
FIG. 1 shows an exemplary medical image system according to the present invention.

An embodiment of the present invention will hereinafter be described with reference to FIGS. 1 to 4. As shown in FIG. 1, imaging diagnostic system 1000 of the embodiment 1 includes injector 100 and CT scanner 300 that serves an imaging diagnostic apparatus. Injector 100 is wire-connected or wirelessly connected to CT scanner 300. The CT scanner 300 includes scanner body 301 and control unit 302.

Figure 2:
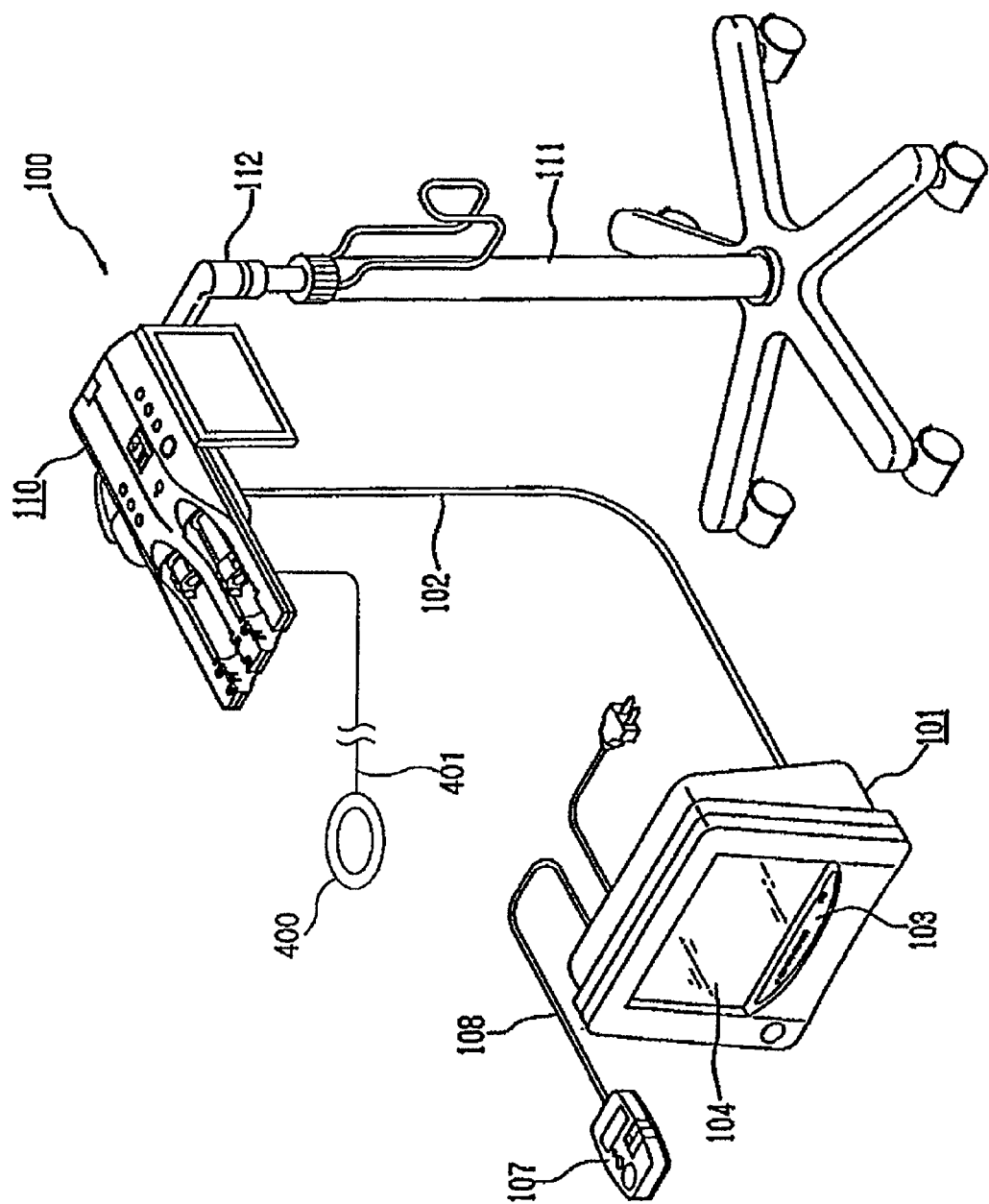
FIG. 2 is a perspective view showing the outer appearance of an exemplary injector.

As shown in FIG. 2, by way of example, injector 100 includes injection head 110 which is attached to an upper portion of arm 112 connected to stand 111. The head 110 is connected to injection control unit 101 formed as a separate component through cable 102. Injection control unit 101 has main operation panel 103, display 104, hand unit 107 connected thereto through cable 108 and the like.

Figure 3:
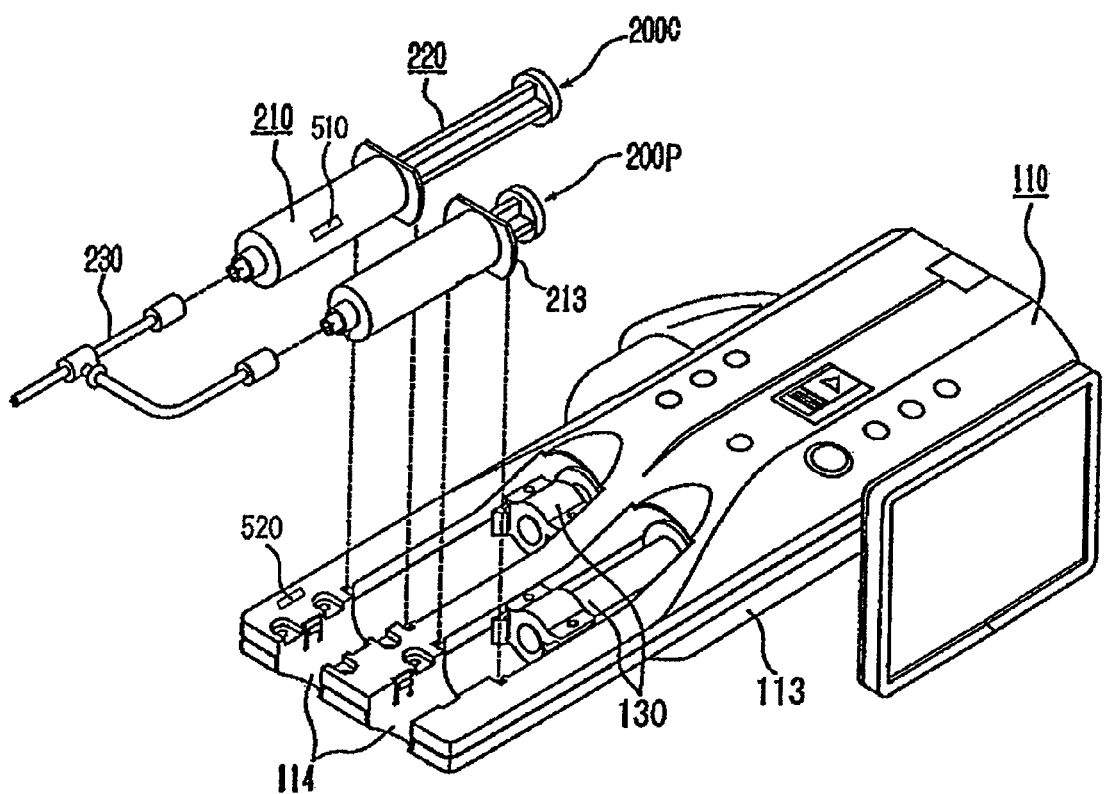
FIG. 3 is a perspective view showing an injection head of the injector.

As shown in FIG. 3, head body 113 of injection head 110 has two concave portions 114 as syringe holding mechanisms formed in its upper surface. Two syringes 200C and 200P are mounted in these concave portions 114. Each of syringes 200C and 200P has cylinder 210 and piston 220. For example, syringe 200C is filled with contrast medium for CT as chemical liquid, while syringe 200P is filled with physiological saline. The ends of the two syringes mounted on head body 113 are connected with connection tube 230. Pistons 220 of the syringes are pushed by piston driving mechanisms 130 movable individually to allow injection of the contrast medium, injection of the physiological saline, and simultaneous injection of both.

The piston driving mechanism, control mechanism and the like can generally be configured by using a known structure.

In Embodiment 1, injector 100 also includes a patient identifying portion 400 as shown in FIG. 2. In a more preferable embodiment, as shown in FIG. 3, data carrier means 510 such as an IC chip (RF tag) for recording syringe information is attached to or embedded in syringe 210. Syringe information receiving means 520 such as an RF communication device for communicating with the data carrier means to receive the syringe information therefrom is embedded in injection head 110.

Figure 4:
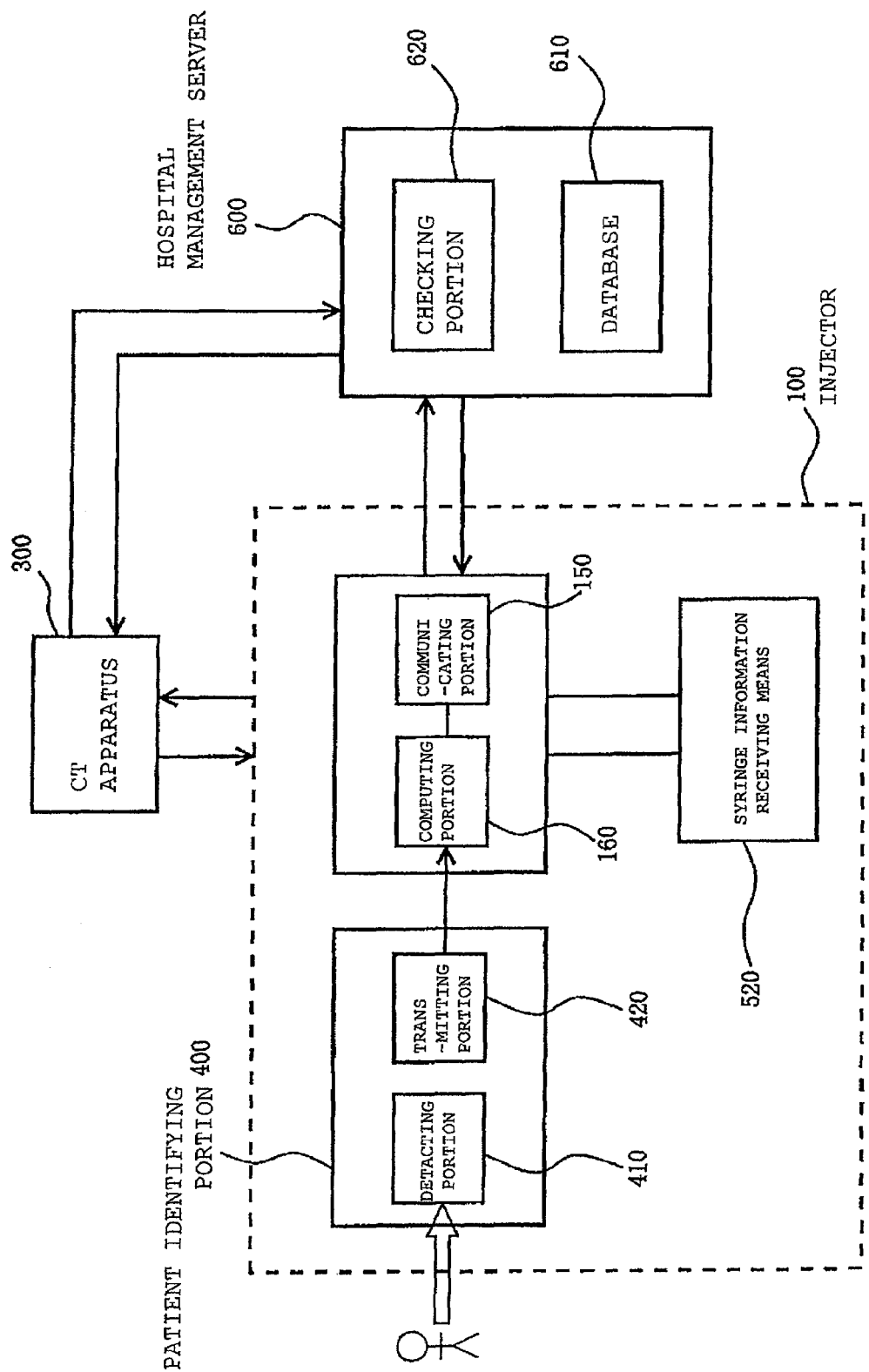
FIG. 4 is a block diagram for explaining the medical image system according to the present invention.

FIG. 4 is a block diagram showing the overall medical image system of Embodiment 1. Patient identifying portion 400 is communicatively connected to injector 100 as part of injector 100. CT apparatus 300 and hospital management server 600 are also communicatively connected to the injector 100.

Patient identifying portion 400 includes transmitting portion 420 serving as an interface for communicating with detecting portion 410 (detecting means) and computing portion 160 in the injector. The detecting portion 410 performs detection or communication for identifying a patient. Detecting portion 410 can be implemented by using various specific apparatuses depending on how to identify a patient. For taking information specific to humans, it is possible to use particularly a fingerprint identifying apparatus, an iris identifying apparatus, a vein identifying apparatus, and a CCD camera, for example. Patient-specific information may be recorded on an item with an IC chip, a barcode, a patient card or the like. In this case, the detecting portion 410 is realized by using a transceiver which can communicate with the IC chip, a barcode reader, or a patient card reader, for example. The information taken by detecting portion 410 is processed by a computer or the like in the patient identifying portion as required and then transmitted to computing portion 160 in the injector body via transmitting portion 420. As shown in FIG. 2, the connection between patient identifying portion 400 and the injector body is achieved such that communication can be performed between patient identifying portion 400 and injection head 110 in a wired manner through cable 401 or wirelessly.

Computing portion 160 may be provided in control unit 101 or injection head 110. It communicates with hospital management server 600 via communicating portion 150. Database 610 for patient charts including information about each patient is stored on hospital management server 600.

In Embodiment 1, checking portion 620 serving as a checking means is provided as a function of the hospital management server. Computing portion 160 in the injector transmits its own apparatus ID and the patient-specific information taken by patient identifying portion 400 together with an instruction for checking to checking means 620 provided for hospital management server 600. Checking means 620 checks database 610 to retrieve a record which matches the patient-specific information from the database. Since details of tests and treatment to be performed on each patient are recorded on database 610, checking means 620 obtains the apparatus ID of the injector and checks if there is any match between the ID and the tests to be performed on the patient.

When a match is found, checking means 620 sends a message indicating the completion of the check to injector 100. Upon reception of the message, injector 100 displays a message indicating the permission of the test or the like on the display or the like and completes the checking.

On the other hand, when no record in database 610 matches the patient-specific information, or when any record in the database matches the patient-specific information but a CT test is not recorded in the tests to be performed on the patient, an alarm of "no match" is displayed and the checking is finished.

It is also preferable that, when no match results from the check, the alarm is issued, transition to the next injection preparation stage is inhibited, and injection condition entry and/or injection start instruction entry is not accepted unless an operator enters a cancel instruction.

In Embodiment 1, syringe-information receiving means 520 may be provided as described above. Data carrier means 510 is implemented by using a barcode and the like as well as the IC chip. Accordingly, syringe-information receiving means 520 is embodied by using a transceiver which can communicate with the IC chip, a barcode reader and the like. The syringe information includes the manufacturer, capacity, product name, and lot number of the syringe, and as required, chemical liquid information such as the type and concentration of the chemical liquid.

The syringe information is sent to computing portion 160, which in turn checks it against the test details of the patient to determine whether or not the syringe is a proper one.

Injector 100 may transmit and receive data about CT imaging conditions and chemical liquid injection conditions to and from CT apparatus 300, or may perform injection in association with the CT imaging.

According to the abovementioned configuration, communication with the hospital management server can be performed via the injector which is certainly placed in a CT test room. This allows easy and reliable patient identification to reduce errors due to manual entry. In addition, the system can be compact as a whole.

<Embodiment 2>

While Embodiment 1 has shown the example in which the checking means is provided for hospital management server 600, the checking means may be provided for injector 100. For example, computing portion 160 (see FIG. 4) described in Embodiment 1 may also serve as the checking means. Checking means 620 provided for the hospital management server in Embodiment 1 is not required in this case.

In Embodiment 2, the ID of a patient (such as his name and a unique number) to be tested is entered or transmitted from the hospital management server to the injector prior to chemical liquid injection, for example. Computing portion 160 receives patient-specific information taken by patient identifying portion 400 similarly to Embodiment 1. Computing portion 160 issues an instruction for transmission of patient-specific information corresponding to the patient ID to hospital server 600. In response thereto, hospital management server 600 transmits the requested patient-specific information corresponding to the patient ID, and, details of tests and details of treatments to be performed on the patient to computing portion 160. Computing portion 160 checks the patient-specific information received from the patient identifying portion 400 against patient-specific information stored on the hospital management server in order to identify the patient. Computing portion 160 also checks whether the details of tests and details of treatments recorded in the data transmitted from the hospital management server match details of tests and details of treatment which will be performed.

When a match is found, injector 100 displays a message indicating the completion of the check, a message indicating the permission of the test and the like on a display or the like and completes the checking.

On the other hand, when no match is found in the patient IDs in the hospital management server, hospital management server 600 notifies injector 100 of the absence of the patient ID, and injector 100 displays an alarm of "no match" and completes the checking.

When the patient-specific information corresponding to the patient ID is received by injector 100 but the details of tests and details of treatments recorded on the hospital management server are different from the details of tests and details of treatments which will be performed, injector 100 display an alarm of "no match" and completes the checking.

It is also preferable that, when no match results from the checking, the alarm is issued, transition to the next injection preparation stage is inhibited, and injection condition entry and/or injection start instruction entry is not accepted unless an operator enters a cancel instruction.

According to the abovementioned configuration, communication with the hospital management server can be performed via the injector which is certainly placed in a CT test room, so that the system can be compact as a whole. In addition, reliable patient identification can be performed.

The structures not described particularly can be formed according to Embodiment 1.

<Embodiment 3>

Embodiments 1 and 2 have described the transmission and reception of the information mainly including the patient-specific information and the data of details of tests and treatment between hospital management server 600 and injector 100.

In addition to the effect described in Embodiments 1 and 2, the medical image system according to the present invention preferably can perform transmission and reception of data described below. The following is an example of an embodiment which includes a data outputting means for transmitting chemical liquid injection data to a hospital management server.

Injector 100 performs chemical liquid injection and then transmits the chemical liquid injection data to the hospital management server via communicating portion 150. The chemical liquid injection data includes data selected from information about a tried chemical liquid (for example, the type, concentration, and manufacturer name of the chemical liquid), injection quantity, injection period, injection speed (particularly, an injection profile representing the injection speed versus the injection period), and injection pressure (particularly, a profile representing the injection pressure versus the injection period). Hospital management server 600 receives and records the data on database 610. On the other hand, medical images taken by CT apparatus 300 are sent to the hospital management server via the injector or directly. The hospital management server 600 records the CT test results on database 610. Thus, the injection conditions are recorded on database 610 together with the CT test results.

The data transmitted from CT apparatus 300 to hospital management server 600 directly or via the injector preferably includes not only the CT images but also imaging condition data (exposure conditions such as a radiation dose and a radiation exposure timing).

Since injector 100 has the data outputting function in this manner, all the injection conditions are stored on the hospital management server. Thus, when a doctor observes and analyzes an image on a monitor communicative with the hospital management server in diagnosis, the injection conditions can be displayed and checked together with the CT images. Therefore, it is possible to easily perform comparison with the injection conditions in the previous test or determination of the injection conditions in the next test.

In recent years, disclosure of medical practice has been needed socially. According to the present invention, such need can be easily addressed, since all the test conditions are managed on the hospital management server in a unified manner.

In the above description, the terms "means" and "portion" forming part of the system according to the present invention may be formed of hardware having a CPU (Central Processing Unit), ROM (Read Only Memory), RAM (Random Access Memory), an I/F (Interface) unit and the like, software for operating the hardware, a sensor and the like, for example. Each of them may be a dedicated mechanism or also serve as another means, or may be a logical configuration on a computer system. Those skilled in the art can readily form the specific structure by referring to the specification.

While the x-ray CT apparatus is used as an example for the description, the present invention is applicable to a different imaging apparatus such as an MRI apparatus, PET apparatus, ultrasonic diagnostic apparatus, CT angiography apparatus, or MRA apparatus. Imaging condition information represents setting conditions specific to each apparatus and is sent as data to the hospital management server. A contrast medium, physiological saline or the like suitable for each apparatus is used as the chemical liquid.

Conventionally known hospital management systems include a medical information system called HIS (Hospital Information System) for reception and accounting processing of outpatients and a radiation diagnosis information system called RIS (Radiology Information System) used in a radiation section. In general, the former is a system for paperwork such as server management of image data, reception work, and diagnostic billing, whereas the RIS is a system for radiation tests and diagnosis. In the present invention, the hospital management server is preferably part of any of the HIS, the RIS, and an in-hospital information system in which these systems are associated.

What is claimed is:

1. A medical image system comprising:
   (i) a medical imaging apparatus;
   (ii) an injector comprising a piston driving mechanism and a control mechanism configured to inject at least contrast medium as chemical liquid into a patient, the piston driving mechanism holding a syringe comprising a cylinder and a syringe piston configured to move the syringe piston relative to the cylinder, and the control mechanism configured to control the piston driving mechanism, wherein the injector comprises:
      (a) a detector configured to detect patient-specific information,
      (b) a receiver configured to receive imaging conditions from the medical imaging apparatus, and
      (c) one or more transmitter(s) configured to transmit patient-specific information, chemical liquid injection data and received imaging condition data to a hospital management server; and
   (iii) a hospital management server, which has a database for patient information, and
   (iv) checking means for providing at least one of the hospital management server and the injector, or being provided as a separate apparatus, wherein the checking means receives information transmitted from the detector, and checks the received information to identify the patient specific to received imaging condition data.

2. The medical image system according to claim 1, wherein the checking means is provided for the hospital management server, the injector transmits the patient-specific information obtained in the patient identifying portion, to the checking means provided for the hospital management server via the communicating means, and the checking means checks the information against the database in order to perform patient identification.

3. The medical image system according to claim 1, wherein the checking means is provided for the injector, the injector receives the patient-specific information from the hospital management server via the communicating means, and the checking means checks the patient-specific information received from the patient identifying portion, against the patient-specific information received from the hospital management server in order to perform patient identification.

4. The medical image system according to claim 1, wherein the syringe comprises a data carrier configured to record syringe information, and the injector comprises a syringe-information receiver configured to receive the syringe information recorded on the data carrier.

5. An injector used in the medical image system according to claim 1.

6. The medical image system according to claim 1, wherein the injector comprises two piston driving mechanisms, configured to be movable individually to allow injection of the contrast medium, injection of the saline and simultaneous injection of both.

* * * * *